(12) United States Patent
Kosuge et al.

(10) Patent No.: US 8,045,772 B2
(45) Date of Patent: Oct. 25, 2011

(54) SYSTEM AND METHOD FOR COMPARING DENTAL X-RAY IMAGES

(75) Inventors: Eiko Kosuge, Takasaki (JP); Koichi Ito, Sendai (JP); Takafumi Aoki, Sendai (JP)

(73) Assignees: Eiko Kosuge, Gunma-Ken (JP); Tohoku University, Miyagi-Ken (JP)

( * ) Notice: Subject to any disclaimer, the term of this patent is extended or adjusted under 35 U.S.C. 154(b) by 784 days.

(21) Appl. No.: 12/165,961

(22) Filed: Jul. 1, 2008

(65) Prior Publication Data

US 2009/0274997 A1  Nov. 5, 2009

(30) Foreign Application Priority Data

May 2, 2008 (JP) .................................. 2008-120622

(51) Int. Cl.
*G06K 9/00* (2006.01)
(52) U.S. Cl. .......................................... 382/128; 378/62
(58) Field of Classification Search .................. 378/62, 378/38, 39, 191; 382/128, 132; 433/215
See application file for complete search history.

(56) References Cited

U.S. PATENT DOCUMENTS 7,027,650 B2 * 4/2006 Williame et al. ............. 382/215
7,245,753 B2 * 7/2007 Squilla et al. ................ 382/128

OTHER PUBLICATIONS

Akira Nikaido et al., "A High-Accuracy Dental Radiograph Registration Algorithm Using Phase-Only Correlation", $22^{nd}$ SIP Symposium of IEICE Technical Group on Signal Processing, pp. 694-699, published on Nov. 7, 2007.
TM Lehmann et al., "Computer-based registration for digital subtraction in dental radiology", Dentomaxillofacial Radiology (2000) 29, pp. 323-346.

* cited by examiner

*Primary Examiner* — Hoon Song
(74) *Attorney, Agent, or Firm* — NDQ&M Watchstone LLP

(57) ABSTRACT

A system for comparing dental X-ray images includes a positional displacement calculator calculating a positional displacement between dental X-ray test and reference images by using phase-only correlation, a positional displacement corrector correcting the positional displacement, a base point extractor defining, as a base image, any one of the dental X-ray test and reference images, and defining, as a corresponding image, the other one of the two dental images, and extracting base points from the base image, a corresponding point extractor extracting corresponding points, which correspond to the base points, from the corresponding image, a correspondence calculator calculating correspondence between the base points and the corresponding points, a nonlinear distortion corrector correcting a nonlinear distortion between the base image and the corresponding image, based on the correspondence, and a similarity calculator finding, by using phase-only correlation, a similarity between the base image and the corresponding image.

21 Claims, 12 Drawing Sheets

$f(n_1,n_2)$    $g(n_1,n_2)$ $fe(n_1,n_2)$    $ge(n_1,n_2)$ f' (n₁,n₂)    g' (n₁,n₂)

□ : BASE POINT f' (n₁,n₂)    g' (n₁,n₂)

□ : BASE POINT    □ : CORRESPONDING POINT

BASE IMAGE f'    CORRESPONDING IMAGE g'
(n₁,n₂)    (n₁,n₂)

BASE IMAGE f'
($n_1, n_2$)

CORRESPONDING IMAGE g'
($n_1, n_2$)

BASE IMAGE f"
($n_1, n_2$)

CORRESPONDING IMAGE g"
($n_1, n_2$)

f''' ($n_1, n_2$)

g''' ($n_1, n_2$)

AFTER DENTAL
TREATMENT

BEFORE DENTAL
TREATMENT

AFTER DENTAL
TREATMENT

BEFORE DENTAL
TREATMENT

AFTER DENTAL
TREATMENT

BEFORE DENTAL
TREATMENT

SYSTEM AND METHOD FOR COMPARING DENTAL X-RAY IMAGES

CROSS REFERENCE TO RELATED APPLICATIONS AND INCORPORATION BY REFERENCE

This application is based upon and claims the benefit of priority from prior Japanese Patent Application P2008-120622 filed on May 2, 2008; the entire contents of which are incorporated by reference herein.

BACKGROUND OF THE INVENTION

1. Field of the Invention

The present invention relates to a method for comparing images, and particularly to a system and method for comparing dental X-ray images.

2. Description of the Related Art

Dental radiographs are used for the purpose of finding a slight change in the internal structure of a bone, monitoring the progress of a disease, developing treatment policies, or determining an identity (see Lehmann, T. M., Grondahl, H. G., & Benn, D. K. (2000). Computer-based registration for digital subtraction in dental radiology. *Dentomaxillofacial Radiology*, 29, 323-346., for example). When dental radiographs are used for any one of these purposes, a radiograph taken several weeks ago or several years ago needs to be accurately compared with a radiograph taken recently. In order to realize a computer-aided diagnosis (CAD) in a dental treatment, it is important that a dental radiograph taken recently should be accurately positioned to a dental radiograph taken in the past. However, because dental radiographs are taken with the films placed in the complicated and narrow oral cavity, a nonlinear distortion exists between the dental radiograph taken recently and the dental radiograph taken in the past, even though the dental radiographs are taken of the same oral cavity of the same person. This brings about a problem that it is difficult to compare the dental radiograph taken recently and the dental radiograph taken in the past.

SUMMARY OF THE INVENTION

An aspect of present invention inheres in a system for comparing dental X-ray images including a positional displacement calculator configured to calculate a positional displacement between a dental X-ray test image and a dental X-ray reference image by using phase-only correlation, a positional displacement corrector configured to correct the positional displacement, a base point extractor configured to define any one of the dental X-ray test image whose positional displacement is corrected and the dental X-ray reference image as a base image, and to define the other one of the two dental images as a corresponding image, as well as to extract multiple base points from the base image, a corresponding point extractor configured to extract multiple corresponding points, which correspond to the multiple base points, from the corresponding image, a correspondence calculator configured to calculate correspondence between the multiple base points and the multiple corresponding points nonlinearly distorted from the multiple base points, a nonlinear distortion corrector configured to correct a nonlinear distortion between the base image and the corresponding image, based on the correspondence, and a similarity calculator configured to find a similarity between the base image whose nonlinear distortion is corrected and the corresponding image by using phase-only correlation.

Another aspect of the present invention inheres in a method for comparing dental X-ray images including calculating a positional displacement between a dental X-ray test image and a dental X-ray reference image by using phase-only correlation, correcting the positional displacement, defining any one of the dental X-ray test image whose positional displacement is corrected and the dental X-ray reference image as a base image, and defining the other one of the two dental images as a corresponding image, as well as extracting multiple base points from the base image, extracting multiple corresponding points, which correspond to the multiple base points, from the corresponding image, calculating correspondence between the multiple base points and the multiple corresponding points nonlinearly distorted from coordinates of the multiple base points, correcting a nonlinear distortion between the base image and the corresponding image, based on the correspondence, and finding a similarity between the base image and the corresponding image between which the nonlinear distortion is corrected by using phase-only correlation.

BRIEF DESCRIPTION OF THE DRAWINGS

FIG. 3 is a first schematic diagram of a tooth which a dental X-ray image according to the embodiment of the present invention is taken of.

FIG. 4 is a second schematic diagram of the tooth which another dental X-ray image according to the embodiment of the present invention is taken of.

FIG. 5 is a third schematic diagram of the tooth which yet another dental X-ray image according to the embodiment of the present invention is taken of.

DETAILED DESCRIPTION OF THE INVENTION

Figure 1:
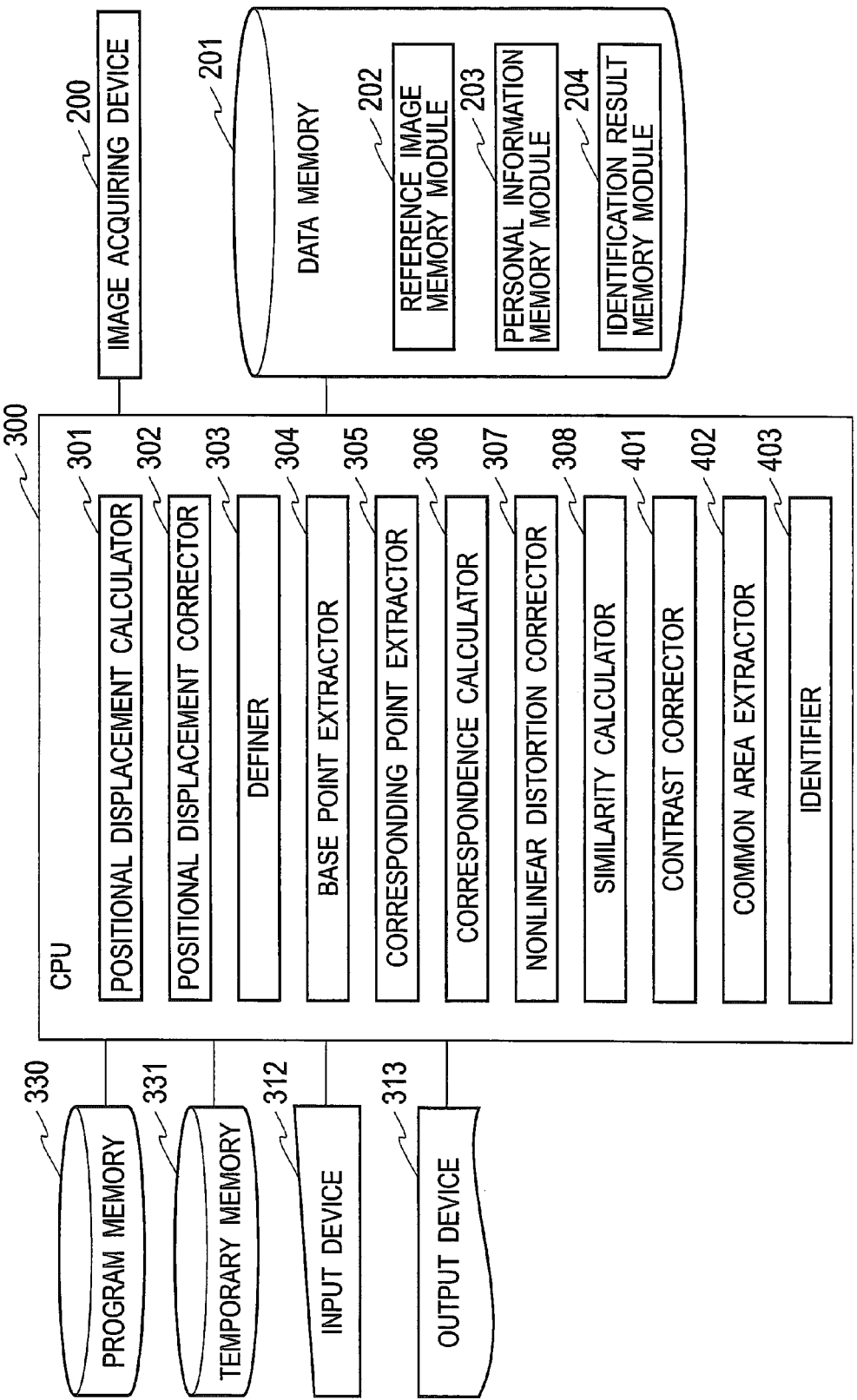
FIG. 1 is a schematic diagram of a system for comparing dental X-ray images according to an embodiment of the present invention.

Descriptions will be provided hereinbelow for an embodiment of the present invention. In descriptions to the following drawings, the same or similar components are denoted by the same or similar reference numerals. It should be noted that the drawings are schematic. For this reason, specific dimensions and the like should be understood with the following descriptions taken into consideration. It goes without saying that the dimensional relationships and ratios among some components are different from one drawing to another.

With reference to FIG. 1, a system for comparing dental X-ray images according to the embodiment of the present invention includes, an image acquiring device 200, such as a scanner, for acquiring a dental X-ray test image that has been taken, and a central processing unit (CPU) 300 connected to the image acquiring device 200. The CPU 300 includes a positional displacement calculator 301 configured to calculate a positional displacement between the dental X-ray test image and a dental X-ray reference image, based on phase-only correlation, and a positional displacement corrector 302 configured to correct the positional displacement between the dental X-ray test image and the dental X-ray reference image.

In addition, the CPU 300 includes a definer 303 configured to define anyone of the dental X-ray test image whose positional displacement is corrected and the dental X-ray reference image as a base image, and to define the other one of the two dental images as a corresponding image, a base point extractor 304 configured to extract multiple base points at each of which a pixel value changes beyond a threshold value, from the base image, and a corresponding point extractor 305 configured to extract multiple corresponding points, which correspond to the multiple base points, from the corresponding image. A same object is recorded at the base point and the corresponding point.

Moreover, the CPU 300 includes a correspondence calculator 306 configured to calculate correspondence between coordinates of the multiple base points and coordinates of the corresponding points which are nonlinearly distorted from the coordinates of the multiple base points, a nonlinear distortion corrector 307 configured to correct a nonlinear distortion between the base image and the corresponding image, based on the correspondence, and a similarity calculator 308 configured to find a similarity between the base image and the corresponding image between which the nonlinear distortion is corrected, based on the phase-only correlation.

Hereinbelow, consider the dental X-ray test image and the dental X-ray reference image as images each with $N_1 \times N_2$ pixels. In addition, the dental X-ray test image is represented with $g(n_1, n_2)$, and the dental X-ray reference image is represented with $f(n_1, n_2)$.

Figure 2:
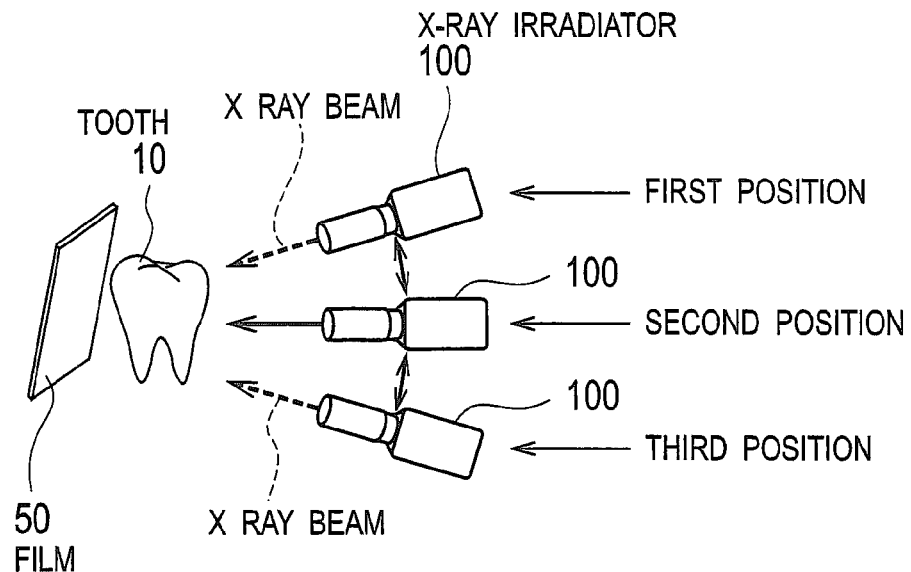
FIG. 2 is a schematic diagram showing how to take dental X-ray images according to the embodiment of the present invention.

As shown in FIG. 2, the dental X-ray test image $g(n_1, n_2)$ is taken by placing a small film 50 behind a tooth 10, and subsequently by placing an X-ray irradiator 100 near the face with the film 50 being held by a finger, as well as thereafter by irradiating an X-ray on the film 50 from the X-ray irradiator 100. A previously acquired dental X-ray reference image $f(n_1, n_2)$ is also taken in the same manner as the dental X-ray test image $g(n_1, n_2)$. For the purpose of taking an idealistic dental X-ray image, it is necessary that the film 50 should be placed, in parallel with the tooth 10, and perpendicularly to the X-ray irradiated on the film 50. However, because the film 50 and the X-ray irradiator 100 are manually placed by a picture taker each time the dental X-ray image is taken, the placement position and angle of each of the film 50 and the X-ray irradiator may vary each time the dental X-ray image is taken. As a result, even though the dental X-ray test image $g(n_1, n_2)$ and the dental X-ray reference image $f(n_1, n_2)$ were taken of the same oral cavity area of the same person, the tooth 10 as the object in the dental X-ray test image may be parallel translated and rotated in comparison with the tooth 10 as the object in the dental X-ray reference image because the dental X-ray test image and the dental X-ray reference image were taken at different times.

Figure 3:
Figure 4:
Figure 5:

For example, the tooth 10 in the dental X-ray image, shown in FIG. 4, which is obtained when the X-ray irradiator 100 is placed in a second position shown in FIG. 2 may be shorter than the tooth 10 in the dental X-ray image, shown in FIG. 3, which is obtained when the X-ray irradiator 100 is placed in a first position shown in FIG. 2. In addition, the tooth 10 in the dental X-ray image, shown in FIG. 5, which is obtained when the X-ray irradiator 100 is placed in a third position shown in FIG. 2 may be far shorter than the tooth 10 in the dental X-ray image, shown in FIG. 4, which is obtained when the X-ray irradiator 100 is placed in the second position shown in FIG. 2.

Figure 6:
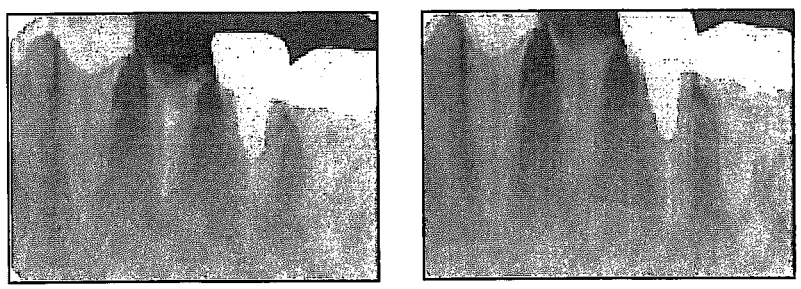
FIG. 6 shows a dental X-ray test image and a dental X-ray reference image according to the embodiment of the present invention.

Furthermore, the distance between the film 50 and the X-ray irradiator 100 may vary each time the dental X-ray image is taken of the tooth 10. For this reason, the tooth 10 as the object in the dental X-ray test image $g(n_1, n_2)$ may be larger or smaller than the tooth 10 as the object in the dental X-ray reference image $f(n_1, n_2)$, because the dental X-ray test image and the dental X-ray reference image were taken at different times. Moreover, because the film 50 is pressed against the tooth 10 with a finger while the dental X-ray image is being taken of the tooth 10, the film 50 may be nonlinearly distorted. The nonlinear distortion of the film 50 may vary each time the dental X-ray image is taken. Additionally, the dental X-ray test image $g(n_1, n_2)$ and the dental X-ray reference image $f(n_1, n_2)$ may be blurred because of noise and the like included while the dental X-ray images are being taken. Examples of the dental X-ray test image $g(n_1, n_2)$ and the dental X-ray reference image $f(n_1, n_2)$ are shown in FIG. 6.

Figure 7:
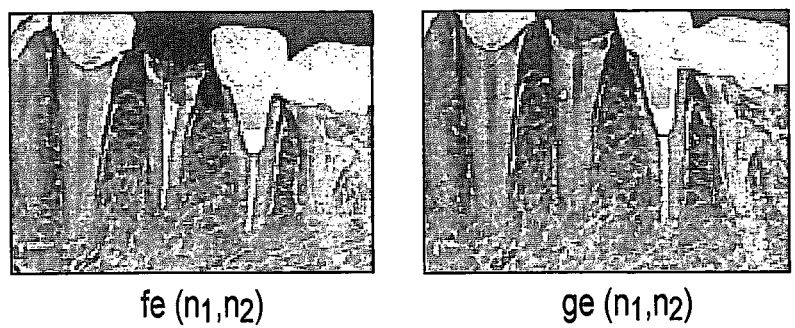
FIG. 7 shows a contrast-corrected dental X-ray test image and a contrast-corrected dental X-ray reference image according to the embodiment of the present invention.

The CPU 300 shown in FIG. 1 further includes a contrast corrector 401. The contrast corrector 401 enhances the contrasts respectively of the dental X-ray test image $g(n_1, n_2)$ and the dental X-ray reference image $f(n_1, n_2)$, and thus generates the contrast-corrected dental X-ray test image $g_e(n_1, n_2)$ and the contrast-corrected dental X-ray reference image $f_e(n_1, n_2)$ which are shown in FIG. 7. The contrast corrector 401 shown in FIG. 1 is designed to enhance a contrast by using LACE (Local Area Contrast Enhancement) and morphological filter. The contrast enhancement of the dental X-ray test image $g(n_1, n_2)$ and the dental X-ray reference image $f(n_1, n_2)$ by the contrast corrector 401 makes it possible to obviously increase the accuracy with which the below-described comparison score is calculated.

The positional displacement calculator 301 calculates the two-dimensional discrete Fourier transform $G_e(k_1, k_2)$ of the contrast-corrected dental X-ray test image $g_e(n_1, n_2)$ by using Equation (1). In the following example, we assume that the index ranges in the discrete space are $n_1 = -M_1, \ldots, M_1$ ($M_1 > 0$) and $n_2 = -M_2, \ldots, M_2$ ($M_2 > 0$) for mathematical simplicity, and hence $N_1 = 2M_1 + 1$ and $N_2 = 2M_2 + 1$. Note that, in the case of the present embodiment, the index ranges in the discrete space are symmetrical between positive and negative numbers. And, the number $N_1$ of vertically-arrayed pixels and the number $N_2$ of horizontally-arrayed pixels are odd numbers, for explanatory convenience. However, it goes without saying that the two-dimensional discrete Fourier transform may be generalized in order that non-negative index ranges can be used, and concurrently in order that the number $N_1$ of vertically-arrayed pixels and the number $N_2$ of horizontally-arrayed pixels can be respectively set at arbitrary positive integers. $G_e(k_1, k_2)$ is given by $$G_e(k_1, k_2) = \sum_{n1=-M1}^{M1} \sum_{n2=-M2}^{M2} g_e(n_1, n_2) W_{N1}^{k1n1} W_{N2}^{k2n2} \quad \text{Equation (1)}$$
$$= A_G(k_1, k_2) e^{j\theta_G(k1,k2)}$$

where $W_{N1} = e^{-j(2\pi/N1)}$ and $W_{N2} = e^{-j(2\pi/N2)}$, and $A_G(k_1, k_2)$ is an amplitude component of the dental X-ray test image $g_e(n_1, n_2)$, as well as $\theta_G(k_1, k_2)$ is a phase component of the dental X-ray test image $g_e(n_1, n_2)$.

In addition, the positional displacement calculator 301 calculates the two-dimensional discrete Fourier transform $F_e(k_1, k_2)$ of the contrast-corrected dental X-ray reference image $f_e(n_1, n_2)$ by use of $$F_e(k_1, k_2) = \sum_{n1=-M1}^{M1} \sum_{n2=-M2}^{M2} f_e(n_1, n_2) W_{N1}^{k1n1} W_{N2}^{k2n2} \quad \text{Equation (2)}$$
$$= A_F(k_1, k_2) e^{j\theta_F(k1,k2)}$$

where $A_F(k_1, k_2)$ is an amplitude component of the dental X-ray reference image $f_e(n_1, n_2)$, and $\theta_F(k_1, k_2)$ is a phase component of the dental X-ray reference image $f_e(n_1, n_2)$.

Thereafter, the positional displacement calculator 301 calculates the square root of the amplitude spectrum of the dental X-ray test image $(|G_e(k_1, k_2)|)^{1/2}$ and the square root of the amplitude spectrum of the dental X-ray reference image $(|F_e(k_1, k_2)|)^{1/2}$. The amplitude spectra are free from the influence of the amount of parallel translation of the object between the dental X-ray test image and the dental X-ray reference image, because the amplitude spectra are influenced by nothing but the rotation angle $\theta$ and the scaling ratio $\kappa$ between the dental X-ray test image and the dental X-ray reference image.

In the case of natural images, almost all of the energy concentrates on a lower frequency range. For this reason, information existing in a higher frequency range generally is enhanced and thus visualized by using the logarithms of the respective amplitude spectra log $\{|G_e(k_1, k_2)|+1\}$ and log $\{|F_e(k_1, k_2)|+1\}$. However, in the case of the dental X-ray images, the amplitude components including information on the magnification, reduction and rotation concentrates on a far lower frequency range than in the case of the general natural images. For this reason, if the amplitude spectra are enhanced by using these logarithms, information with a lower signal-to-noise ratio (SN ratio) is far enhanced. This reduces the accuracy with which the rotation angle $\theta$ and the scaling ratio $\kappa$ are estimated. By contrast, use of the square roots of the respective amplitude spectra makes it possible to smoothly enhance the amplitude spectra of the dental X-ray images from the lower frequency range to the higher frequency range.

Subsequently, the positional displacement calculator 301 computes the log-polar transform (or the Fourier-Mellin transform) of the square root $(|G_e(k_1, k_2)|)^{1/2}$ of the amplitude spectrum of the dental X-ray test image, and thus calculates $G_{LF}(k_1', k_2')$. In addition, the positional displacement calculator 301 computes the log-polar transform (or the Fourier-Mellin transform) of the square root $(|F_e(k_1, k_2)|)^{1/2}$ of the amplitude spectrum of the dental X-ray test image, and thus calculates $F_{LP}(k_1', k_2')$ Where $k_1'$ and $k_2'$ are indices of the dental X-ray images to which the log-polar transform is applied.

Thereafter, the positional displacement calculator 301 calculates the normalized cross power spectrum $R_{FlpGlp}(k_1', k_2')$ of $F_{LP}(k_1', k_2')$ and $G_{LP}(k_1', k_2')$. $RF_{FlpGlp}(k_1', k_2')$ is given by $$R_{FlpGlp}(k_1', k_2') = \frac{F_{Lp}(k_1', k_2') \overline{G_{LP}(k_1', k_2')}}{|F_{LP}(k_1', k_2') \overline{G_{LP}(k_1', k_2')}|} \quad \text{Equation (3)}$$
$$= e^{j\theta(k_1', k_2')}$$

where $\theta(k_1', k_2') = \theta_{Flp}(k_1', k_2') - \theta_{Glp}(k_1', k_2')$, and $\overline{G_{LP}(k_1', k_2')}$ is the complex conjugate of $G_{LP}(k_1', k_2')$.

Subsequently, the positional displacement calculator 301 calculates the band-limited phase-only correlation (BLPOC) function $r_{FlpGlp}^{K1K2}(n_1, n_2)$ as the two-dimensional inverse discrete Fourier transform of the normalized cross power spectrum $R_{FlpGlp}(k_1', k_2')$. $r_{FlpGlp}^{K1K2}(n_1, n_2)$ is given by $$r_{FlpGlp}^{K1K2}(n_1, n_2) = \quad \text{Equation (4)}$$
$$\frac{1}{L_1 L_2} \sum_{k1'=-K1}^{K1} \sum_{k2'=-K2}^{K2} R_{FlpGlp}(k_1', k_2') \times W_{L_1}^{-k_1' n_1} W_{L_2}^{-k_2' n_2}$$

where $K_1 (0 < K_1 \leq M_1)$ and $K_2 (0 < K_2 \leq M_2)$ are effective bands of the two-dimensional inverse discrete Fourier transform, as well as $L_1 = 2K_1 + 1$ and $L_2 = 2K_2 + 1$. In addition, for example, $K_1/M_1 = 0.2$ and $K_2/M_2 = 0.2$.

The use of the band-limited phase-only correlation function limits the two-dimensional inverse discrete Fourier transform of the normalized cross power spectrum $R_{FlpGlp}(k_1', k_2')$ in the effective bands of the image texture, and thus concentrates the energy of the correlation peak. This makes it possible to enhance the image identification performance while eliminating the influence of the high-frequency components with a lower reliability. In addition, the use of the band-limited phase-only correlation function makes the size of the two dimensional inverse discrete Fourier transform smaller than the use of the phase-only correlation function, thus reducing the amount of calculation. In spite of this size reduction, the accuracy with which the positional displacement is estimated by using the band-limited phase-only correlation function is almost equal to the accuracy with which the positional displacement is estimated by using the phase-only correlation function.

The positional displacement calculator 301 detects the location of the correlation peak of the band-limited phase-only correlation function $r_{FlpGlp}^{K1K2}(n_1, n_2)$, and thus calculates the rotation angle θ of the dental X-ray test image $g_e(n_1, n_2)$ to the dental X-ray reference image $f_e(n_1, n_2)$ and the scaling ratio κ of the dental X-ray test image $g_e(n_1, n_2)$ to the dental X-ray reference image $f_e(n_1, n_2)$. The positional displacement corrector 302 corrects the dental X-ray test image $g_e(n_1, n_2)$ in order that the rotation angle θ of the dental X-ray test image $g_e(n_1, n_2)$ to the dental X-ray reference image $f_e(n_1, n_2)$ can be equal to 0 (zero), and concurrently in order that the scaling ratio κ of the dental X-ray test image $g_e(n_1, n_2)$ to the dental X-ray reference image $f_e(n_1, n_2)$ can be equal to 1 (one). Thereby, the positional displacement corrector 302 generates a dental X-ray test image $g_{eκθ}(n_1, n_2)$ which results from correcting the rotation angle θ and the scaling ratio κ.

Subsequently, the positional displacement calculator 301 calculates a band-limited phase-only correlation function $r_{fegeκθ}^{K1K2}(n_1, n_2)$ between the contrast-corrected dental X-ray reference image $f_e(n_1, n_2)$ and the dental X-ray test image $g_{eκθ}(n_1, n_2)$ which results from correcting the contrast, the rotation angle θ and the scaling ratio κ. In this respect, $K_1/M_1=0.5$ and $K_2/M_2=0.5$, for example. Thereafter, the positional displacement calculator 301 detects the location of the correlation peak of the band-limited phase-only correlation function $r_{fegeκθ}^{K1K2}(n_1, n_2)$, and thus calculates the amount of parallel translation of the dental X-ray test image $g_{eκθ}(n_1, n_2)$ to the dental X-ray reference image $f_e(n_1, n_2)$.

Figure 8:
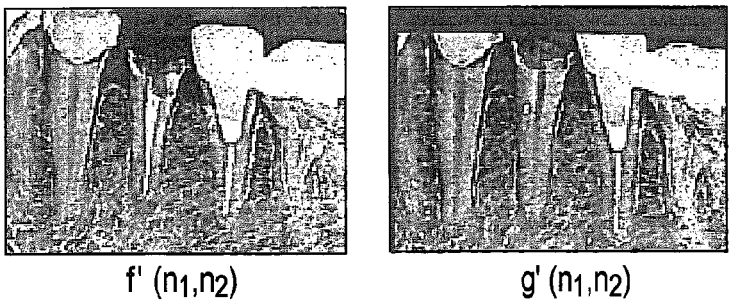
FIG. 8 shows a dental X-ray test image, and a dental X-ray reference image, which result from correcting a rotation angle, a scaling ratio and the amount of parallel translation according to the embodiment of the present invention.

The positional displacement corrector 302 corrects the dental X-ray test image $g_{eκθ}(n_1, n_2)$ which results from correcting the rotation angle θ and the scaling ratio κ in order that the amount of parallel translation of the dental X-ray test image $g_{eκθ}(n_1, n_2)$ to the dental X-ray reference image $f_e(n_1, n_2)$ can be equal to 0 (zero), and thus generates a dental X-ray test image $g'(n_1, n_2)$ and a dental X-ray reference image $f'(n_1, n_2)$, shown in FIG. 8, which result from correcting their respective rotation angles θ, scaling ratios κ and amounts of parallel translation.

Figure 9:
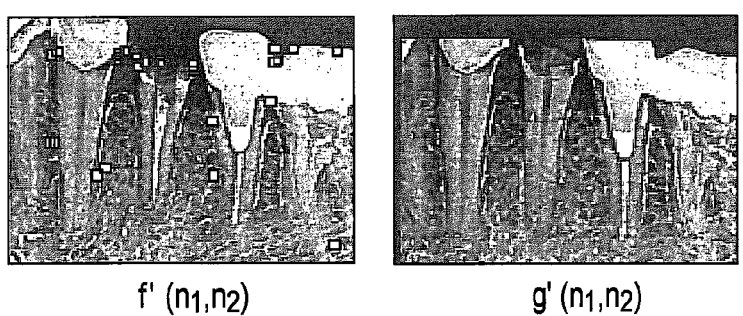
FIG. 9 shows a base image from which multiple base points are extracted and a corresponding image according to the embodiment of the present invention.

The definer 303 shown in FIG. 1 defines any one of the dental X-ray test image $g'(n_1, n_2)$ and the dental X-ray reference image $f'(n_1, n_2)$, which are shown in FIG. 8, as a base image, and defines the other one of the two dental X-ray images as a corresponding image. The following descriptions will be provided with an assumption that the dental X-ray reference image $f'(n_1, n_2)$ is defined as the base image whereas the dental X-ray test image $g'(n_1, n_2)$ is defined as the corresponding image. As shown in FIG. 9, the base point extractor 304 shown in FIG. 1 extracts multiple base points from the base image $f'(n_1, n_2)$ by using the Harris corner detector for detecting an abrupt change in the pixel values (or the brightness value). For the Harris corner detector, consider a matrix Q given by $$Q = \begin{vmatrix} \left[\frac{\partial I}{\partial n_1}\right]^2 & \frac{\partial I}{\partial n_1}\frac{\partial I}{\partial n_2} \\ \frac{\partial I}{\partial n_1}\frac{\partial I}{\partial n_2} & \left[\frac{\partial I}{\partial n_2}\right]^2 \end{vmatrix} \qquad \text{Equation (5)}$$

where the pixel value at a point $(n_1, n_2)$ is $I(n_1, n_2)$.

When two eigenvalues of the matrix Q is large at a point in the base image $f'(n_1, n_2)$, a corner exists there. A corner detector function E is given by $$E = detQ - l(trQ)^2 \qquad \text{Equation (6)}$$

where l is an adjustment parameter. A corner exists at a point to which Equation (6) gives the locally largest values. In some cases, there are very many points to which Equation (6) gives the locally largest values in the base image $f'(n_1, n_2)$. With this taken into consideration, the base point extractor 304 is designed to extract points, to which the largest values not smaller than a predetermined threshold value are give, as the base point. In this respect, a set of "B" base points extracted from the base image $f'(n_1, n_2)$ is represented with $U=(u_1^*, u_2^*, \ldots, u_B^*)^T$.

Figure 10:
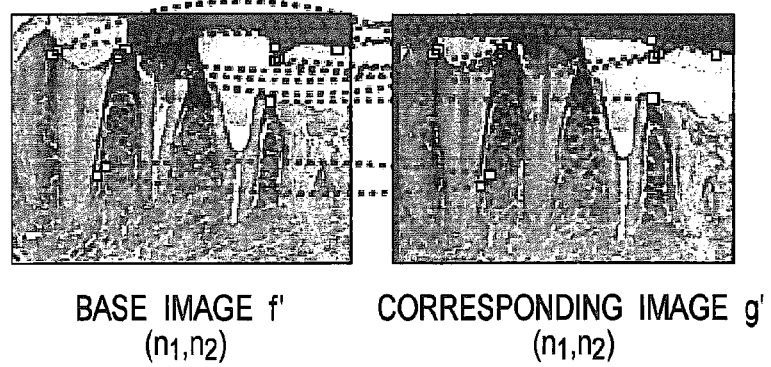
FIG. 10 shows the base image and the corresponding image in which multiple corresponding points are found according to the embodiment of the present invention.

The corresponding point extractor 305, shown in FIG. 1, applies sub-pixel corresponding point search to a local image block around each of the multiple base points, and thus finds corresponding points in the corresponding image $g'(n_1, n_2)$ as shown in FIG. 10. Specifically, the corresponding point extractor 305, shown in FIG. 1, generates a rough base image $f'(n_1, n_2)$, which is rougher than the base image $f'_m(n_1, n_2)$ by "m" degrees, in accordance with $$f'_m(n_1, n_2) = \frac{1}{4}\sum_{p1=0}^{m}\sum_{p2=0}^{m} f'_{m-1}(2n_1 + p_1, 2n_2 + p_2) \qquad \text{Equation (7)}$$

where m is an integer, and the base image $f'(n_1, n_2)$ is represented as $f'_0(n_1, n_2)$.

In addition, the corresponding point extractor 305 generates a rough corresponding image $g'_m(n_1, n_2)$, which is rougher than the corresponding image $g'(n_1, n_2)$ by "m" degrees, in accordance with $$g'_m(n_1, n_2) = \frac{1}{4}\sum_{p1=0}^{m}\sum_{p2=0}^{m} g'_{m-1}(2n_1 + p_1, 2n_2 + p_2) \qquad \text{Equation (8)}$$

where the corresponding image $g'(n_1, n_2)$ is represented as $g'_0(n_1, n_2)$.

In Equations (7) and (8), the largest value of m is set at 2, for example. Subsequently, the corresponding point extractor 305 calculates a rough base point $u_m=(u_{m\,1}, u_{m\,2})$ in the rough base image $f'_m(n_1, n_2)$, which corresponds to a base point $u=u_0=(u_1, u_2)$ in the base image $f'_0(n_1, n_2)$, in accordance with $$u_m=[(½)u_{m-1}]=([(½)u_{m-1\cdot 1}],[(½)u_{m-1\cdot 2}]) \qquad \text{Equation (9)}$$

where [x] means that the fractional part of x is rounded off.

Furthermore, when "m" takes on its maximum, the corresponding point extractor 305 assumes that the coordinate of the rough corresponding point $v_m$ in the rough corresponding image $g'_m(n_1, n_2)$ is equal to the coordinate of the rough base point $u_m$ in the rough base image $f'_m(n_1, n_2)$.

Subsequently, the corresponding point extractor 305 extracts a sub rough base image $f'_{m-1sub}(n_1, n_2)$ with the center on the rough base point $u_{m-1}$ from the rough base image $f'_{m-1}(n_1, n_2)$. In addition, the corresponding point extractor 305 extracts a sub rough corresponding image $g'_{m-1sub}(n_1, n_2)$ around a coordinate $2v_m$ from the rough corresponding image $g'_{m-1}(n_1, n_2)$. The size of each of the sub rough base image $f'_{m-1sub}(n_1, n_2)$ and the sub rough corresponding image $g'_{m-1sub}(n_1, n_2)$ is 32×32 pixels, for example.

Thereafter, the corresponding point extractor 305 calculates a positional displacement between the sub rough base image $f'_{m-1sub}(n_1, n_2)$ and the sub rough corresponding image $g'_{m-1sub}(n_1, n_2)$ by using the window function and the phase-only correlation function given by $$w(n_1, n_2) = \frac{1 + \cos(\pi n_1 / M_1)}{2} \frac{1 + \cos(\pi n_2 / M_2)}{2}. \quad \text{Equation (10)}$$

Note that the use of the window function solves the discontinuity of the image ends.

When the calculated positional displacement vector is denoted by $\delta_{m-1}$, a rough corresponding point $v_{m-1}$ in the sub rough corresponding image $g'_{m-1sub}(n_1, n_2)$, which corresponds to the rough base point $u_{m-1}$ in the sub rough base image $f'_{m-1sub}(n_1, n_2)$, is given by $$v_{m-1} = 2v_m + \delta_{m-1}. \quad \text{Equation (11)}$$

The corresponding point extractor 305 calculates a rough corresponding point $v_0$ by sequentially decreasing "m" one-by-one from its maximum. When, for example, the maximum of "m" is equal to 2, the corresponding point extractor 305 calculates a rough base point $u_2=(u_{2\ 1}, u_{2\ 2})$ in a rough base image $f'_2(n_1, n_2)$ by using Equation (9), and thus assumes that a rough corresponding point $v_2$ in a rough corresponding image $g'_2(n_1, n_2)$ is equal to $u_2$. Subsequently, the corresponding point extractor 305 extracts a sub rough base image $f'_{1sub}(n_1, n_2)$ with the center thereof on a rough base point $u_1$ from a rough base image $f'_1(n_1, n_2)$, and extracts a sub rough corresponding image $g'_{1sub}(n_1, n_2)$ with the center thereof on a point $2v_2$ from a rough corresponding image $g'_1(n_1, n_2)$. In addition, the corresponding point extractor 305 calculates a positional displacement $\delta_1$ between the sub rough base image $f'_{1sub}(n_1, n_2)$ and the sub rough corresponding image $g'_{1sub}(n_1, n_2)$ by using the window function and the phase-only correlation function, and calculates a rough corresponding point $v_1$ by using Equation (11).

Thereafter, the corresponding point extractor 305 extracts a sub base image $f'_{0sub}(n_1, n_2)$ around a base point $u_0$ from a base image $f'_0(n_1, n_2)$, and extracts a sub corresponding image $g'_{0sub}(n_1, n_2)$ around a point $2v_1$ from a corresponding image $g'_0(n_1, n_2)$. Furthermore, the corresponding point extractor 305 calculates a positional displacement $\delta_0$ between the sub base image $f'_{0sub}(n_1, n_2)$ and the sub corresponding image $g'_{0sub}(n_1, n_2)$ by using the window function and the phase-only correlation function, and calculates a rough corresponding point $v_0 = v = (v_1, v_2)$ by using Equation (11). The calculated rough corresponding point $v_0 = v = (v_1, v_2)$ in the corresponding image $g'_0(n_1, n_2)$ includes no pixel-level error.

Thereafter, the corresponding point extractor 305 extracts the sub base image $f'_{0sub}(n_1, n_2)$ around a base point $u=u_0=(u_1, u_2)$ from the base image $f'_0(n_1, n_2)$. In addition, the corresponding point extractor 305 extracts the sub corresponding image $g'_{0sub}(n_1, n_2)$ around the rough corresponding point $v_0 = v = (v_1, v_2)$ calculated from the corresponding image $g'_0(n_1, n_2)$ at a pixel-level. In this respect, $n_1 = -M_{1sub}, \ldots, M_{1sub}(M_{1sub} > 0)$, $n_2 = -M_{2sub}, \ldots, M_{2sub}$ $(M_{2sub} > 0)$, $N_{1sub} = 2M_{1sub} + 1$, and $N_{2sub} = 2M_{2sub} + 1$.

Furthermore, the corresponding point extractor 305 defines an initial window function $w_f(n_1, n_2)$ for the sub base image $f'_{0sub}(n_1, n_2)$ and an initial window function $w_g(n_1, n_2)$ for the sub corresponding image $g'_{0sub}(n_1, n_2)$. A window function $w(x_1, x_2)$ corresponding to all of the real variables $x_1$ and $x_2$ is given by $$w(x_1, x_2) = \frac{1 + \cos(\pi x_1 / M_{1sub})}{2} \frac{1 + \cos(\pi x_2 / M_{2sub})}{2} \quad \text{Equation (12)}$$

where $w_f(n_1, n_2) = w_g(n_1, n_2) = w(x_1, x_2)|_{x_1=n_1, x_2=n_2}$.

Instead of the Hanning window function given by Equation (12), the Hamming, Gaussian or Kaiser window function can be used.

Thereafter, the corresponding point extractor 305 calculates a positional displacement $\delta = (\delta_1, \delta_2)$ between the sub base image $f'_{0sub}(n_1, n_2)$ and the sub corresponding image $g'_{0sub}(n_1, n_2)$ by using the initial window function and the phase-only correlation function. In this respect, when a fine positional displacement $\delta = (\delta_1, \delta_2)$ between the sub base image $f'_{0sub}(n_1, n_2)$ and the sub corresponding image $g'_{0sub}(n_1, n_2)$ is represented with $\delta = (\delta_1, \delta_2)$, the phase-only correlation function of the sub base image $f'_{0sub}(n_1, n_2)$ and the sub corresponding image $g'_{0sub}(n_1, n_2)$ is modeled by $$r(n_1, n_2) \approx \quad \text{Equation (13)}$$

$$\frac{\alpha}{N_{1sub} N_{2sub}} \frac{\sin\{\pi(n_1 + \delta_1)\}}{\sin\left\{\frac{\pi}{N_{1sub}}(n_1 + \delta_1)\right\}} \frac{\sin\{\pi(n_2 + \delta_2)\}}{\sin\left\{\frac{\pi}{N_{2sub}}(n_2 + \delta_2)\right\}}$$

where $\alpha=1$. $\alpha$ is a parameter introduced to represent the height of the correlation peak. $\alpha$ is actually not larger than 1 (one), because the value of $\alpha$ decreases when uncorrelated noise is added to the images. By fitting the correlation peak model given by Equation (13) to the numeric data of the actually computed phase-only correlation function, it is possible to estimate the peak location existing between the pixels, and accordingly to estimate the parameters $\alpha$, $\delta_1$ and $\delta_2$. The estimated $\delta_1$ and $\delta_2$ are smaller than 1 (one), and are at a sub-pixel level. Furthermore, the corresponding point extractor 305 updates the window functions $w_f(n_1, n_2)$ and $w_g(n_1, n_2)$, with the positional displacement $\delta = (\delta_1, \delta_2)$ calculated at a sub-pixel level, by use of $$w_f(n_1, n_2) = w\left[x_1 + \frac{\delta_1}{2}, x_2 + \frac{\delta_2}{2}\right]\bigg|_{x_1=n_1, x_2=n_2} \quad \text{Equation (14)}$$

and $$w_g(n_1, n_2) = w\left[x_1 - \frac{\delta_1}{2}, x_2 - \frac{\delta_2}{2}\right]\bigg|_{x_1=n_1, x_2=n_2}. \quad \text{Equation (15)}$$

Subsequently, the corresponding point extractor 305 repeats the calculation of the positional displacement $\delta = (\delta_1, \delta_2)$ by using the updated window functions and the phase-only correlation function. The number of times the corresponding point extractor 305 repeats the calculation is five, for example. Each time the calculation of the positional displacement $\delta = (\delta_1, \delta_2)$ is repeated, the sub-pixel-level error becomes smaller. Thereafter, the corresponding point extractor 305 adds the positional displacement $\delta = (\delta_1, \delta_2)$ to the rough corresponding point $v_0 = v = (v_1, v_2)$ as shown by $$v_{0F} = v_0 + \delta \quad \text{Equation (16)}$$

and thus calculates a corresponding point $v_{0F}$ in the corresponding image $g'(n_1, n_2)$.

In this respect, a set of "B" corresponding points found in the corresponding image $g'(n_1, n_2)$ is represented with $V=(v_1^*, v_2^*, \ldots, v_B^*)^T$. Note that the corresponding point extractor 305 is designed to find a corresponding point for each of the multiple base points. However, if the correlation peak value of the phase-only correlation function is smaller than the threshold value, the corresponding points thus found are eliminated as false corresponding points. The threshold value is 0.4, for example.

The correspondence calculator 306, shown in FIG. 1, holds the thin plate spline (TPS) function given by $$v = TPS(u) = d + A \cdot u + C^T \cdot s(u) \quad \text{Equation (17)}$$

where "u" denotes a pixel in the base image f'($n_1$, $n_2$), "v" denotes a pixel in the corresponding image g'($n_1$, $n_2$), "d" denotes a 2×1 translation vector, "A" denotes a 2×2 affine translation matrix, and "C" denotes a "B×2" coefficient matrix. In addition, $s(u) = (\sigma(u - u_1^*), \sigma(u - u_2^*), \ldots, \sigma(u - u_B^*))^T$. $\sigma(u)$ is represented with $$\sigma(u) = \begin{cases} \|u\|^2 \log(\|u\|) & \|u\| > 0 \\ 0 & \|u\| = 0. \end{cases} \quad \text{Equation (18)}$$

Equation (17) has 2B+6 parameters. The correspondence calculator 306 substitutes a set $U = (u_1^*, u_2^*, \ldots, u_B^*)^T$ of "B" base points and a set $V = (v_1^*, v_2^*, \ldots, v_B^*)^T$ of "B" corresponding points into Equation (19), and finds 2B+6 parameters by solving Equation (19) using least square method.

$$\begin{bmatrix} H & l_B & U \\ l_B^T & 0 & 0 \\ U^T & 0 & 0 \end{bmatrix} \begin{bmatrix} C \\ d^T \\ A^T \end{bmatrix} = \begin{bmatrix} V \\ 0 \\ 0 \end{bmatrix} \quad \text{Equation (19)}$$

where $1_B$ denotes a vector consisting of "1" with a length "B", "H" denotes a B×B matrix with an element $h_{ij} = \sigma(u_i^* - u_j^*)$. Subsequently, the correspondence calculator 306 solves Equation (19) by using the method of least square, and thereby finds 2B+6 parameters.

Figure 11:
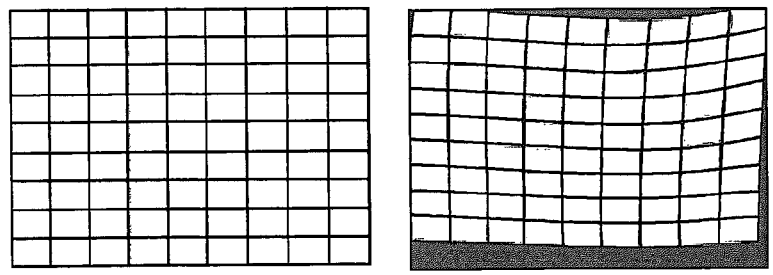
FIG. 11 shows grids on a corresponding image which results from correcting a nonlinear distortion from the base image according to the embodiment of the present invention.
Figure 12:
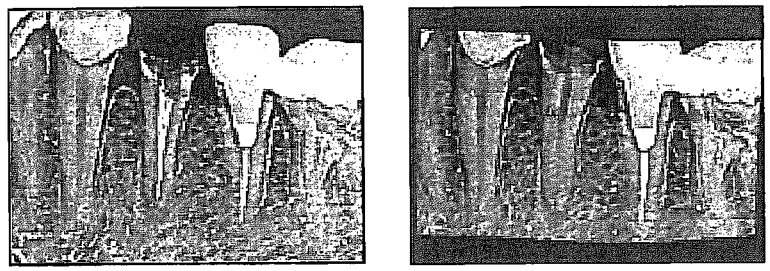
FIG. 12 shows the corresponding image which results from correcting the nonlinear distortion from the base image according to the embodiment of the present invention.

The correspondence calculator 306 substitutes the 2B+6 parameters thus found into Equation (17), and calculates the thin plate spline function representing correspondence between the multiple base points included in the base image and the multiple corresponding points included in the corresponding image. The nonlinear distortion corrector 307 transforms the corresponding image g'($n_1$, $n_2$), as shown by grids in FIG. 11, by using the thin plate spline function representing the correspondence between the multiple base points included in the base image and the multiple corresponding points included in the corresponding image. Thereafter, the nonlinear distortion corrector 307, shown in FIG. 1, converts all of the coordinates constituting the corresponding image g'($n_1$, $n_2$), based on the Equation (17) into which the parameters are substituted, and thus generates a corresponding image g''($n_1$, $n_2$) which results from correcting its nonlinear distortion from the base image f'($n_1$, $n_2$), as shown in FIG. 12.

Figure 13:
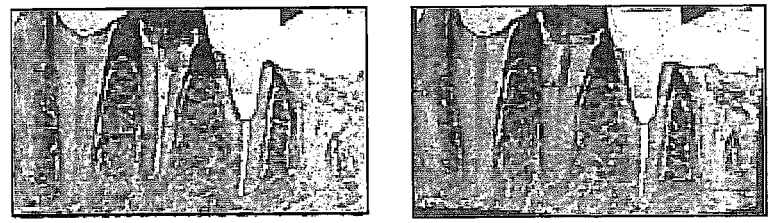
FIG. 13 shows a base image and a corresponding image from which common areas are extracted according to the embodiment of the present invention.

The CPU 300, shown in FIG. 1, further includes a common area extractor 402. An area and coordinates which is included in any one of the base image f'($n_1$, $n_2$) and the corresponding image g''($n_1$, $n_2$) but not in the other one of the two images represent noise components uncorrelated to the phase-only correlation function. As shown in FIG. 13, the common area extractor 402 extracts a common area between the base image f'($n_1$, $n_2$) and the corresponding image g''($n_1$, $n_2$) which results from correcting its nonlinear distortion from the base image f'($n_1$, $n_2$), and thus generates a common area f'''($n_1$, $n_2$) extracted from the base image f'($n_1$, $n_2$) and a common area g'''($n_1$, $n_2$) extracted from the corresponding image g''($n_1$, $n_2$). The common area extractor 402 extracts the common areas by using a pixel projection in an $n_1$ direction and a pixel projection in an $n_2$ direction, respectively. The size of the common area f'''($n_1$, $n_2$) extracted from the base image f'($n_1$, $n_2$) is equal to the size of the common area g'''($n_1$, $n_2$) extracted from the corresponding image g''($n_1$, $n_2$).

The similarity calculator 308, shown in FIG. 1, calculates the band-limited phase-only correlation function of the common area f'''($n_1$, $n_2$) and the common area g'''($n_1$, $n_2$) with a condition of, for example, $K_1/M_1 = K_2/M_2 = 0.1$. Furthermore, the similarity calculator 308 finds the largest peak value of the band-limited phase-only correlation function as a comparison score for indicating a similarity between the dental X-ray test image g($n_1$, $n_2$) and the dental X-ray reference image f($n_1$, $n_2$). The CPU 300 further includes an identifier 403. If a comparison score indicating a similarity between the dental X-ray test image g($n_1$, $n_2$) of a photographed person who is not identified and the dental X-ray reference image f($n_1$, $n_2$) of a photographed person which is identified is higher than a threshold value, the identifier 403 identifies the person of whom the dental X-ray test image g($n_1$, $n_2$) is taken as the person of whom the dental X-ray reference image f($n_1$, $n_2$) is taken.

A data memory 201 is connected to the CPU 300. The data memory 201 includes a reference image memory module 202, a personal information memory module 203 and an identification result memory module 204. The dental X-ray reference image f($n_1$, $n_2$) is stored in the reference image memory module 202. Information on a person whom the dental X-ray reference image f($n_1$, $n_2$) has been taken of is stored in the personal information memory module 203. A result of identification carried out by the identifier 403 is stored in the identification result memory module 204.

An input device 312, an output device 313, a program memory 330 and a temporary memory 331 are further connected to the CPU 300. Examples of what is usable as the input device 312 include a keyboard and a pointing device such as a mouse. Examples of what is usable as the output device 313 include image displaying devices such as a liquid crystal display and a monitor, and a printer. An operating system and the like for controlling the CPU 300 are stored in the program memory 330. Results of arithmetic performed by the CPU 300 are sequentially stored in the temporary memory 331. Examples of what are usable as the program memory 330 and the temporary memory 331 include storage media, such as a semiconductor memory, a magnetic disc, an optical disc, a magneto-optical disc and a magnetic tape, in which a program is stored.

Figure 14:
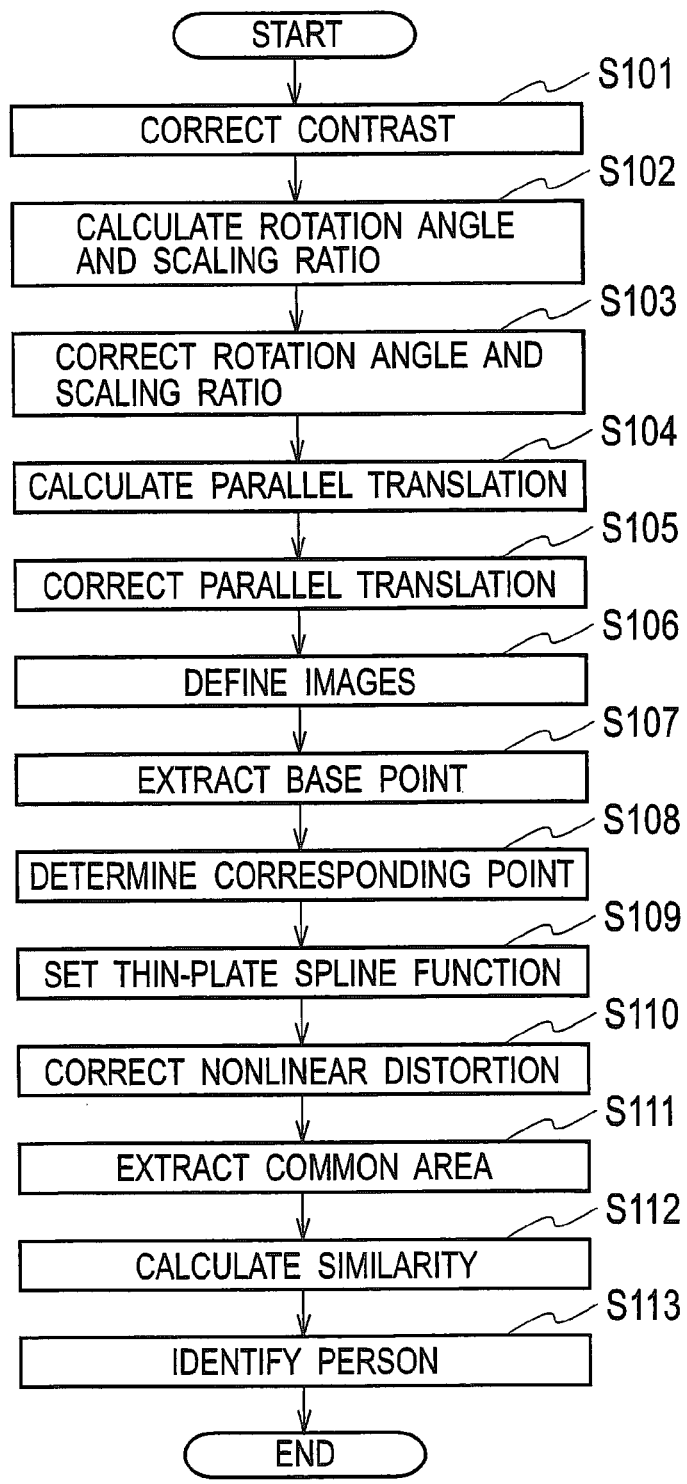
FIG. 14 is a flowchart showing a method for comparing dental X-ray images according to the embodiment of the present invention.

Next, descriptions will be provided for a method for comparing dental X-ray images according to the embodiment by using a flowchart shown in FIG. 14. It should be noted that results of arithmetic performed by the CPU 300 shown in FIG. 1 are sequentially stored in the temporary memory 331.

In step S101, the contrast corrector 401 reads the dental X-ray test image g($n_1$, $n_2$), shown in FIG. 6, through the image acquiring device 200. In addition, the contrast corrector 401, shown in FIG. 1, reads the dental X-ray reference image f($n_1$, $n_2$), shown in FIG. 6, which has been saved in the reference image memory module 202. Subsequently, the contrast corrector 401 generates a contrast-corrected dental X-ray test image $g_e(n_1, n_2)$ and a contrast-corrected dental X-ray reference image $f_e(n_1, n_2)$, which are shown in FIG. 7. Thereafter, the contrast corrector 401, shown in FIG. 1, transmits the contrast-corrected dental X-ray test image $g_e(n_1, n_2)$ and the contrast-corrected dental X-ray reference image $f_e(n_1, n_2)$ to the positional displacement calculator 301.

In step S102, the positional displacement calculator 301 calculates the two-dimensional discrete Fourier transforms $G_e(k_1, k_2)$ and $F_e(k_1, k_2)$ respectively of the dental X-ray test image $g_e(n_1, n_2)$ and the dental X-ray reference image $f_e(n_1, n_2)$ in accordance with Equations (1) and (2). Subsequently, the positional displacement calculator 301 calculates $G_{LP}(k_1', k_2')$ resulting from the log-polar transform of the square root of the amplitude spectrum of the dental X-ray test image $(|G_e(k_1, k_2)|)^{1/2}$ and $F_{LP}(k_1', k_2')$ resulting from the log-polar transform of the square root of the amplitude spectrum of the dental X-ray reference image $(|F_e(k_1, k_2)|)^{1/2}$. Thereafter, the positional displacement calculator 301 calculates the normalized cross power spectrum $R_{FlpGlp}(k_1', k_2')$ in accordance with Equation (3), and thereafter calculates the band-limited phase-only correlation function $r_{FlpGlp}^{K1K2}(n_1, n_2)$ in accordance with Equation (4).

In step S103, the positional displacement calculator 301 calculates the rotation angle $\theta$ of the dental X-ray test image $g_e(n_1, n_2)$ to the dental X-ray reference image $f_e(n_1, n_2)$ and the scaling ratio $\kappa$ of the dental X-ray test image $g_e(n_1, n_2)$ to the dental X-ray reference image $f_e(n_1, n_2)$, based on the location of the correlation peak of the band-limited phase-only correlation function $r_{FlpGlp}^{K1K2}(n_1, n_2)$, and transmits the rotation angle $\theta$ and the scaling ratio $\kappa$ to the positional displacement corrector 302. The positional displacement corrector 302 corrects the dental X-ray test image $g_e(n_1, n_2)$ in order that the rotation angle $\theta$ can become equal to 0 (zero) and in order that the scaling ratio $\kappa$ can become equal to 1 (one), and thus generates the dental X-ray test image $g_{e\kappa\theta}(n_1, n_2)$ which results from correcting the rotation angle $\theta$ and the scaling ratio $\kappa$. The positional displacement corrector 302 transmits the corrected dental X-ray test image $g_{e\kappa\theta}(n_1, n_2)$ to the positional displacement calculator 301.

In step S104, the positional displacement calculator 301 calculates the band-limited phase-only correlation function $r_{fege\kappa\theta}^{K1K2}(n_1, n_2)$ between the contrast-corrected dental X-ray reference image $f_e(n_1, n_2)$ and the dental X-ray test image $g_{e\kappa\theta}(n_1, n_2)$ which results from correcting the contrast, the rotation angle $\theta$ and the scaling ratio $\kappa$. Subsequently, the positional displacement calculator 301 calculates the amount of parallel translation of the dental X-ray test image $g_{e\kappa\theta}(n_1, n_2)$ which results from correcting the rotation angle $\theta$ and the scaling ratio $\kappa$ of the dental X-ray test image to the dental X-ray reference image $f_e(n_1, n_2)$, based on the location of the correlation peak. Thereafter, the positional displacement calculator 301 transmits the amount of parallel translation thus calculated to the positional displacement corrector 302.

In step S105, the positional displacement corrector 302 generates the dental X-ray test image $g'(n_1, n_2)$ and the dental X-ray reference image $f'(n_1, n_2)$, shown in FIG. 8, to which a correction is applied in order that their respective amount of parallel translation can become equal to 0 (zero). The positional displacement corrector 302, shown in FIG. 1, transmits the generated dental X-ray test image $g'(n_1, n_2)$ and the generated dental X-ray reference image $f'(n_1, n_2)$ to the definer 303. In step S106, the definer 303 defines the dental X-ray reference image $f'(n_1, n_2)$ as the base image, and defines the dental X-ray test image $g'(n_1, n_2)$ as the corresponding image. It should be noted that the definer 303 may define the dental X-ray reference image $f'(n_1, n_2)$ as the corresponding image, and the dental X-ray test image $g'(n_1, n_2)$ as the base image. Subsequently, the definer 303 transmits the base image $f'(n_1, n_2)$ to the base point extractor 304, and transmits the corresponding image $g'(n_1, n_2)$ to the corresponding point extractor 305. In step S107, as shown in FIG. 9, the base point extractor 304 extracts the set $U=(u_1^*, u_2^*, \ldots, u_B^*)^T$ of "B" base points from the base image $f'(n_1, n_2)$ by using the Harris corner detection using Equations (5) and (6) or the like. Thereafter, the base point extractor 304, shown in FIG. 1, transmits the base image $f'(n_1, n_2)$ and the set $U=(u_1^*, u_2^*, \ldots, u_B^*)^T$ of the base points to the corresponding point extractor 305.

In step S108, the corresponding point extractor 305 calculates the multiple rough corresponding points which respectively correspond to the multiple base points extracted from the base image $f'(n_1, n_2)$ by using Equations (7) to (11). Subsequently, the corresponding point extractor 305 calculates the positional displacement $\delta=(\delta_1, \delta_2)$ between the sub base image $f'_{0sub}(n_1, n_2)$ around each base point and the sub corresponding image $g'_{0sub}(n_1, n_2)$ around each rough corresponding point by using the initial window function given by Equation (12) and the phase-only correlation function. Thereafter, the corresponding point extractor 305 updates the window functions $w_f(n_1, n_2)$ and $w_g(n_1, n_2)$ as shown by Equations (14) and (15), and thus repeats the calculation of the positional displacement $\delta=(\delta_1, \delta_2)$, and accordingly determines the corresponding point corresponding to the base point. The corresponding point extractor 305 determines the corresponding point for each of the base points, and thus determines the set $V=(v_1^*, v_2^*, \ldots, v_B^*)^T$ of the B corresponding points, which corresponds to the set $U=(u_1^*, u_2^*, \ldots, u_B^*)^T$ of the base points, in the corresponding image $g'(n_1, n_2)$, as shown in FIG. 10. After that, the corresponding point extractor 305, shown in FIG. 1, transmits the set $U=(u_1^*, u_2^*, \ldots, u_B^*)^T$ of the base points and the set $V=(v_1^*, v_2^*, \ldots, v_B^*)^T$ of the corresponding points to the correspondence calculator 306.

In step S109, the correspondence calculator 306 finds the 2B+6 parameters of the thin-plate spline function given by Equation (17) by using the set $U=(u_1^*, u_2^*, \ldots, u_B^*)^T$ of the base points and the set $V=(v_1^*, v_2^*, \ldots, v_B^*)^T$ of the corresponding points in accordance with Equation (19). Subsequently, the correspondence calculator 306 substitutes the 2B+6 parameters thus found into Equation (17). Thereafter, the correspondence calculator 306 transmits the thin-plate spline function into which the 2B+6 parameters are substituted to the nonlinear distortion corrector 307. In step S110, the nonlinear distortion corrector 307 converts all of the coordinates constituting the corresponding image $g'(n_1, n_2)$, based on the Equation (17) into which the 2B+6 parameters are substituted, and thus generates the corresponding image $g''(n_1, n_2)$ which results from correcting the nonlinear distortion of the corresponding image $g'(n_1, n_2)$ to the base image $f'(n_1, n_2)$, as shown in FIG. 12. After that, the nonlinear distortion corrector 307, shown in FIG. 1, transmits the corresponding image $g''(n_1, n_2)$, which results from correcting the nonlinear distortion of the corresponding image $g'(n_1, n_2)$, to the common area extractor 402. In step S111, as shown in FIG. 13, the common area extractor 402 generates the common area $f'''(n_1, n_2)$ extracted from the base image $f'(n_1, n_2)$ and the common area $g'''(n_1, n_2)$ extracted from the corresponding image $g''(n_1, n_2)$. The nonlinear distortion corrector 307, shown in FIG. 1, transmits the common area $f'''(n_1, n_2)$ and the common area $g'''(n_1, n_2)$ to the similarity calculator 308.

In step S112, the similarity calculator 308 finds the largest peak value of the band-limited phase-only correlation function of the common area $f'''(n_1, n_2)$ and the common area $g'''(n_1, n_2)$ as the comparison score for indicating the similarity between the dental X-ray test image $g(n_1, n_2)$ and the dental X-ray reference image $f(n_1, n_2)$. Subsequently, the similarity calculator 308 transmits the comparison score to the identifier 403. In step S113, the identifier 403 reads from the personal information memory module 203 the information on the person of whom the dental X-ray reference image $f(n_1, n_2)$ has been taken. Thereafter, the identifier 403 identifies the person of whom the dental X-ray test image $g(n_1, n_2)$ has been taken as the person of whom the dental X-ray reference image $f(f_1, f_2)$ has been taken, when the comparison score is higher than the threshold value. After that, the identifier 403 stores in the identification result memory module 204 the information that the person of whom the dental X-ray test image $g(n_1, n_2)$ has been taken is identified as the person of whom the dental X-ray reference image $f(f_1, f_2)$ has been taken. With this, the identifier 402 ends the method of comparing dental X-ray images according to the embodiment.

The above-described system and method for comparing dental X-ray images, according to the embodiment, make it possible to compare the dental X-ray test image $g(n_1, n_2)$ and the dental X-ray reference image $f(f_1, f_2)$ with a higher accuracy, even in a case where a nonlinear distortion exists between the dental X-ray test image $g(n_1, n_2)$ and the dental X-ray reference image $f(f_1, f_2)$.

EXAMPLE

Figure 15:
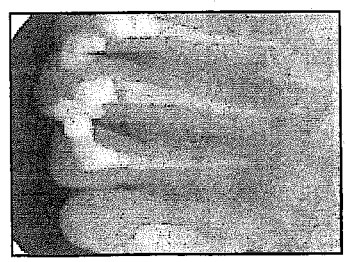
FIG. 15 shows first dental radiographs respectively taken before and after a dental treatment according to an example of the embodiment of the present invention.
Figure 15:
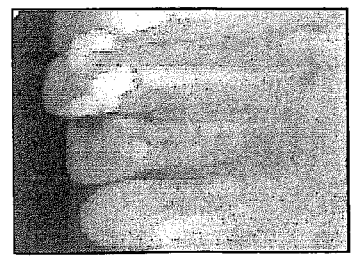
Figure 16:
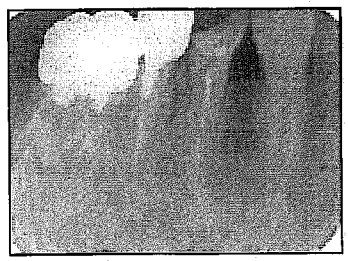
FIG. 16 shows second dental radiographs respectively taken before and after a dental treatment according to the example of the embodiment of the present invention.
Figure 16:
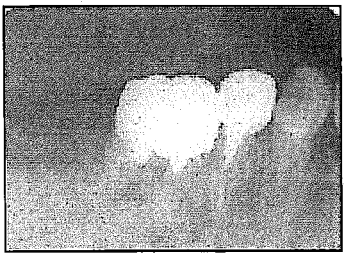
Figure 17:
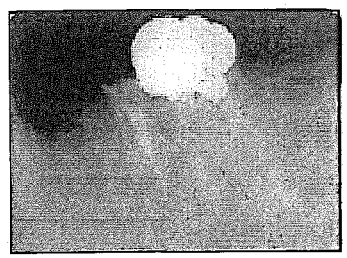
FIG. 17 shows third dental radiographs respectively taken before and after a dental treatment according to the example of the embodiment of the present invention.
Figure 17:
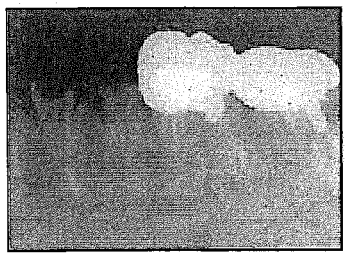

Similarities were evaluated between dental radiographs taken before the respective dental treatments and dental radiographs taken after the respective dental treatments by using a database which stores dental radiographs taken before and after dental treatments. For this example, the database was constructed as follows. A dental radiograph (with 367× 485 pixels) was taken of each of 250 patients before their dental treatments. A week or more later than their dental treatments, another dental radiograph (with 367×485 pixels) was taken of each of the same 250 patients. The total of 500 radiographs (250 patients×2 radiographs) were stored in the database. Note that, because each dental radiograph has a margin in each side, an image with 307×425 pixels obtained by excluding 30 pixels in each side was used for each dental radiograph. Each of FIGS. 15, 16 and 17 shows examples respectively of a dental radiograph taken before a dental treatment and another dental radiograph taken after the dental treatment, which were stored in the database.

The method for comparing dental X-ray images according to the embodiment and two methods each of comparing dental X-ray images according to comparative examples were used for the similarity evaluation. In the case of the comparing method according to the first comparative example, a correction was applied to the dental radiographs taken before and after the dental treatments in terms of a rotation angle θ, a scaling ratio κ and the amount of parallel translation only, but not in terms of a nonlinear distortion. In the case of the comparing method according to the second comparative example, a correction was applied to the dental radiographs taken before and after the dental treatments in terms of a rotation angle θ, a scaling ratio κ and the amount of parallel translation, and subsequently another correction was applied to the same dental radiographs in terms of a nonlinear distortion by using the projection transform.

For quantitative evaluation of the positioning accuracy, verification was made on a 1-to-n basis. In addition, the dental radiographs taken after the respective treatments were defined as "dental X-ray test images," and the dental radiographs taken before the respective treatment which were stored in the database were defined as "dental X-ray reference images." One "dental X-ray test image" was compared with the 250 "dental X-ray reference images." Thereby, the comparison score was calculated for each paired dental X-ray images. This process was applied to all of the "dental X-ray test images."

Figure 18:
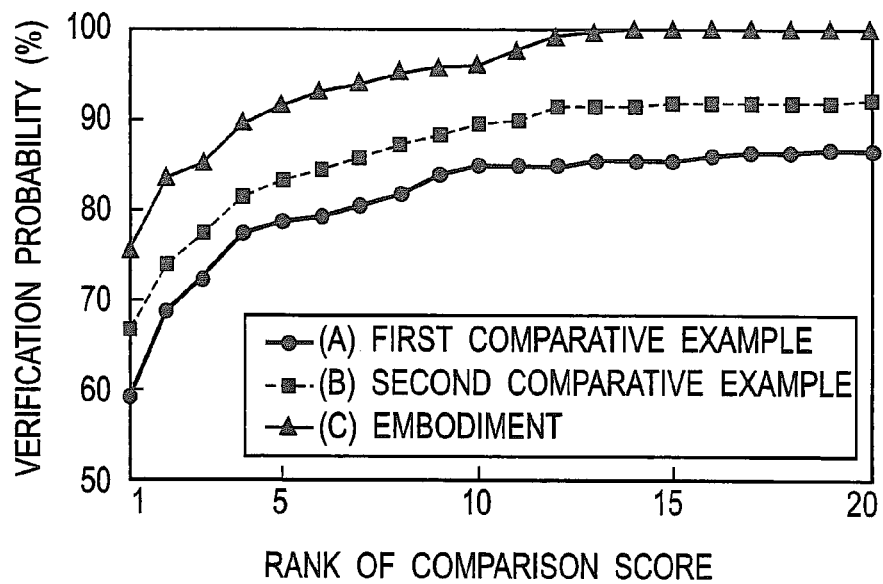
FIG. 18 is a graph showing a cumulative match curve according to the example of the embodiment of the present invention.

Subsequently, the rank of each comparison score was plotted on the horizontal axis. At each rank, a verification probability representing a probability that the "dental X-ray test image" and the "dental X-ray reference image" may be taken of the same person was plotted on the vertical axis. Thereby, a cumulative match curve (CMC) shown in FIG. 18 was obtained as follows. The cumulative match curve is a scheme for evaluating the performance of the 1-to-n verification. A higher verification probability with a higher comparison score means that the images were correctly matched.

When the method for comparing dental X-ray images according to the embodiment was used, the probability that a pair of the "dental X-ray test image" and the "dental X-ray reference image" both taken of the same person recorded the first highest comparison score was 75.6% (=189/250). In contrast, when the method according to the first comparative example was used, the probability that a pair of the "dental X-ray test image" and the "dental X-ray reference image" both taken of the same person recorded the first highest comparison score was 59.2% (=148/250). When the method according to the second comparative example was used, the probability that a pair of the "dental X-ray test image" and the "dental X-ray reference image" both taken of the same person recorded the first highest comparison score was 66.8% (=167/250).

Furthermore, when the method for comparing dental X-ray images according to the embodiment was used, all of the pairs each consisting of the "dental X-ray test image" and the "dental X-ray reference image" both taken of the same person were able to be included in the pairs which recorded the first to 14th highest comparison scores for each dental X-ray test image. By contrast, when the methods according to the first and second comparative examples were used, not all of the pairs each consisting of the "dental X-ray test image" and the "dental X-ray reference image" both taken of the same person were able to be included in the pairs which recorded the first to 20th highest comparison scores for each dental X-ray test image.

Figure 19:
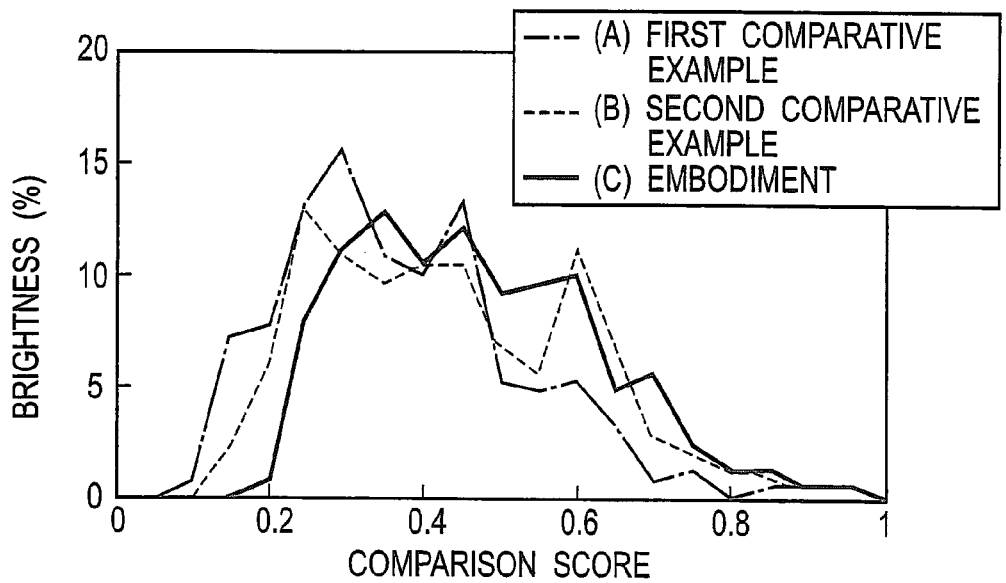
FIG. 19 is a graph showing frequencies of comparison scores according to the example of the embodiment of the present invention.
Figure 20:
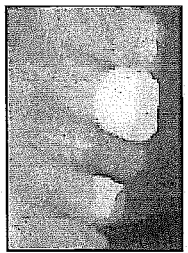
FIG. 20 shows a first comparison result according to the example of the embodiment of the present invention.
Figure 21:
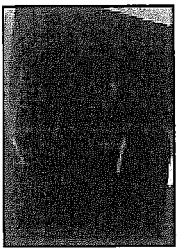
FIG. 21 shows a second comparison result according to the example of the embodiment of the present invention.
Figure 22:
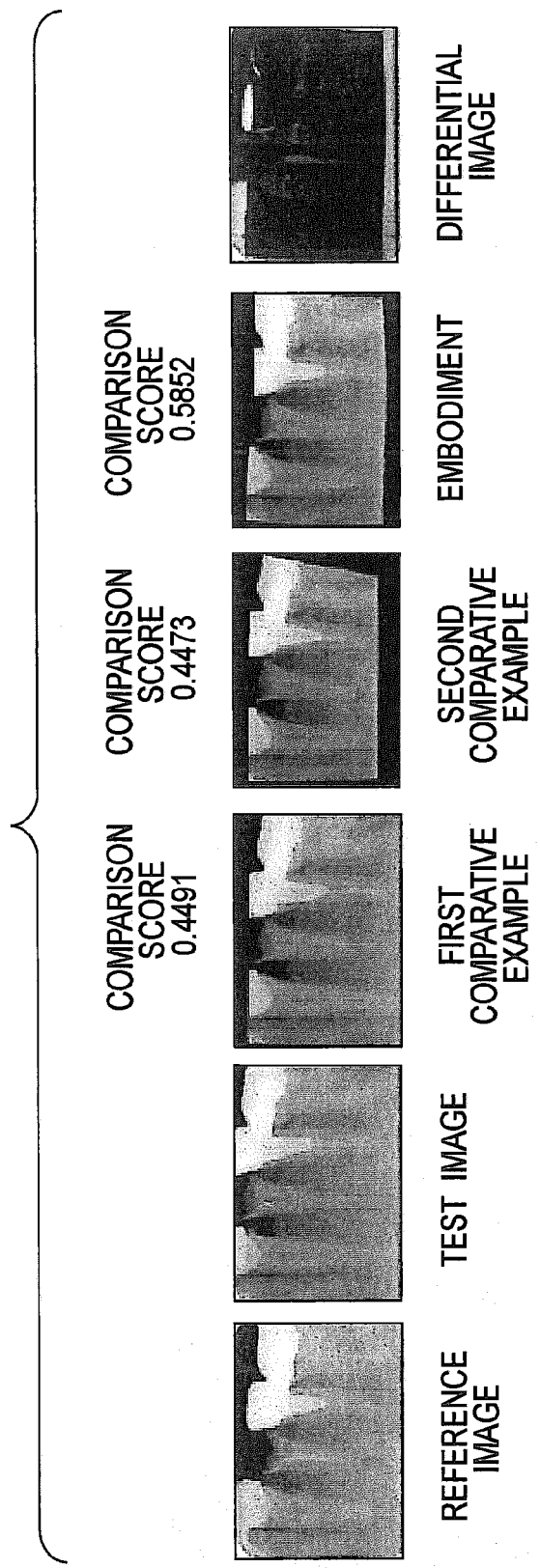
FIG. 22 shows a third comparison result according to the example of the embodiment of the present invention.
Figure 23:
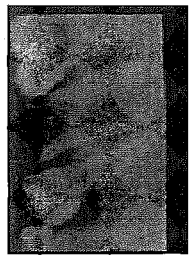
FIG. 23 shows a fourth comparison result according to the example of the embodiment of the present invention.

Moreover, as shown in FIG. 19, generally, the comparison score of each paired "dental X-ray test image" and "dental X-ray reference image" both taken of the same person was higher when the method of comparing dental X-ray images according to the embodiment was used than when the methods according to the first and second comparative examples were used.

FIGS. 20 to 23 each show the "dental X-ray reference image", the "dental X-ray test image," a "dental X-ray test image" corrected by using the method according to the first comparative example, a "dental X-ray test image" corrected by using the method according to the second comparative example, a "dental X-ray test image" and "dental X-ray reference image" corrected by using the method of comparing dental X-ray images according to the embodiment, as well as a differential image of the "dental X-ray test image" corrected by using the method of comparing dental X-ray images according to the embodiment. As shown in FIGS. 20 to 23, the use of the method of comparing dental X-ray images according to the embodiment made the comparison score higher than the use of any other method.

Other Embodiments

The foregoing descriptions have been provided for the present invention citing the embodiment. However, the descriptions and drawings constituting this disclosure should not be understood as limiting the present invention. From this disclosure, various alternative embodiments, examples and operational techniques will be clear to those skilled in the art. For example, it is possible to identify the unidentified dead body with a higher accuracy by taking a dental X-ray test image g($n_1$, $n_2$) of the dead body, and thus by comparing the dental X-ray test image g($n_1$, $n_2$) with dental X-ray reference images f($n_1$, $n_2$) taken of identified persons. It should be understood that, in this manner, the present invention includes various embodiments and the like which have not been described herein. For this reason, the present invention is limited only by appropriate matters defining the invention in the scope of claims.

What is claimed is:

1. A system for comparing dental X-ray images comprising:
    a positional displacement calculator configured to calculate a positional displacement between a dental X-ray test image and a dental X-ray reference image, by using phase-only correlation;
    a positional displacement corrector configured to correct the positional displacement;
    a base point extractor configured to define, as a base image, any one of the dental X-ray test image and the dental X-ray reference image between which the positional displacement is corrected, to define, as a corresponding image, the other one of the two dental images, and to extract a plurality of base points from the base image;
    a corresponding point extractor configured to extract a plurality of corresponding points, which correspond to the plurality of base points, from the corresponding image;
    a correspondence calculator configured to calculate correspondence between the plurality of base points and the plurality of corresponding points nonlinearly distorted from the plurality of base points;
    a nonlinear distortion corrector configured to correct a nonlinear distortion between the base image and the corresponding image, based on the correspondence; and
    a similarity calculator configured to find, by using phase-only correlation, a similarity between the base image and the corresponding image between which the nonlinear distortion is corrected.

2. The system of claim 1, wherein the correspondence is given by a thin plate spline function.

3. The system of claim 1, wherein a pixel value changes beyond a threshold value at each of the plurality of base points.

4. The system of claim 1, wherein the phase-only correlation is a band-limited phase-only correlation function.

5. The system of claim 1, further comprising a contrast corrector configured to correct a contrast of the dental X-ray test image.

6. The system of claim 1, further comprising a contrast corrector configured to correct a contrast of the dental X-ray reference image.

7. The system of claim 1, further comprising a common area extractor configured to extract a common area between the base image and the corresponding image between which the nonlinear distortion is corrected.

8. The system of claim 1, wherein
    a person whom the dental X-ray test image has been taken of is unidentified, and
    a person whom the dental X-ray reference image has been taken of is identified.

9. The system of claim 8, further comprising a personal information memory module configured to store information on the person whom the dental X-ray reference image has been taken of.

10. The system of claim 9, further comprising an identifier configured to identify the person whom the dental X-ray test image has been taken of as the person whom the dental X-ray reference image has been taken of when the base image and the corresponding image are similar to each other.

11. The system of claim 1, wherein the similarity calculator uses, as a comparison score, a maximum peak value of the phase-only correlation function used for the phase-only correlation.

12. A method for comparing dental X-ray images including:
    calculating a positional displacement between a dental X-ray test image and a dental X-ray reference image, by using phase-only correlation;
    correcting the positional displacement;
    defining, as a base image, any one of the dental X-ray test image and the dental X-ray reference image between which the nonlinear distortion is corrected, and defining, as a corresponding image, the other one of the two dental images, as well as extracting a plurality of base points from the base image;
    extracting a plurality of corresponding points, which correspond to the plurality of base points, from the corresponding image;
    calculating correspondence between the plurality of base points and the plurality of corresponding points nonlinearly distorted from coordinates of the plurality of base points;
    correcting a nonlinear distortion between the base image and the corresponding image, based on the correspondence; and
    finding, by using phase-only correlation, a similarity between the base image and the corresponding image between which the nonlinear distortion is corrected.

13. The method of claim 12, wherein the correspondence is given by a thin plate spline function.

14. The method of claim 12, wherein a pixel value changes beyond a threshold value at each of the plurality of base points.

15. The method of claim 12, wherein the phase-only correlation is a band-limited phase-only correlation function.

16. The method of claim 12 further including correcting a contrast of the dental X-ray test image.

17. The method of claim 12 further including correcting a contrast of the dental X-ray reference image.

18. The method of claim 12 further including extracting a common area between the base image and the corresponding image between which the nonlinear distortion is corrected.

19. The method of claim 12, wherein
    a person whom the dental X-ray test image has been taken of is unidentified, and
    a person whom the dental X-ray reference image has been taken of is identified.

20. The method of claim 19 further including identifying the person whom the dental X-ray test image has been taken of as the person whom the dental X-ray reference image has been taken of when the base image and the corresponding image are similar to each other.

21. The method of claims 12 to 20, wherein, in the similarity finding step, a maximum peak value of the phase-only correlation function used for the phase-only correlation is used as a comparison score.

* * * * *